United States Patent
Stroelin (10) Patent No.: US 12,336,866 B2
(45) Date of Patent: Jun. 24, 2025

(54) OPERATING LAMP ASSEMBLY COMPRISING AN AUTOMATICALLY ORIENTABLE CAMERA

(71) Applicant: Karl Leibinger Asset Management GmbH & Co. KG, Mühlheim / Donau (DE)

(72) Inventor: Joachim Stroelin, Rietheim-Weilheim (DE)

(73) Assignee: KARL LEIBINGER ASSET MANAGEMENT GMBH & CO. KG, Mühlheim An der Donau (DE)

( * ) Notice: Subject to any disclaimer, the term of this patent is extended or adjusted under 35 U.S.C. 154(b) by 497 days.

(21) Appl. No.: 17/661,874

(22) Filed: May 3, 2022

(65) Prior Publication Data

US 2022/0354612 A1    Nov. 10, 2022

(30) Foreign Application Priority Data

May 4, 2021   (DE) ..................... 10 2021 111 459.4

(51) Int. Cl.
| | |
|---|---|
| *A61B 90/00* | (2016.01) |
| *A61B 90/35* | (2016.01) |
| *F21V 21/15* | (2006.01) |
| *F21V 21/26* | (2006.01) |
| *F21W 131/205* | (2006.01) |

(52) U.S. Cl.
CPC ............ *A61B 90/361* (2016.02); *A61B 90/35* (2016.02); *F21V 21/15* (2013.01); *F21V 21/26* (2013.01); *A61B 2090/3612* (2016.02); *A61B 2090/373* (2016.02); *F21W 2131/205* (2013.01)

(58) Field of Classification Search
CPC .. F21W 2131/205; A61B 90/30; A61B 90/36; A61B 90/361; A61B 2090/3612
See application file for complete search history.

(56) References Cited

U.S. PATENT DOCUMENTS

| | | | |
|---|---|---|---|
| 2010/0081887 A1 | 4/2010 | Marka et al. | |
| 2020/0237452 A1 | 7/2020 | Wolf et al. | |
| 2021/0302808 A1* | 9/2021 | Watson | G03B 30/00 |

FOREIGN PATENT DOCUMENTS

| | | |
|---|---|---|
| DE | 19843288 A1 | 3/2000 |
| DE | 10063380 A1 | 6/2002 |
| DE | 102011007201 A1 | 5/2012 |
| DE | 102020114426 A1 | 12/2021 |
| EP | 1217292 A1 | 6/2002 |
| EP | 2169965 A1 | 3/2010 |

* cited by examiner

*Primary Examiner* — Sean P Gramling
(74) *Attorney, Agent, or Firm* — McCoy Russell LLP (57) ABSTRACT

The present disclosure relates to an operating lamp assembly which comprises at least one operating lamp for illuminating an operating field, having at least one camera for acquiring an image of the operating field. The operating lamp assembly comprises a controller which automatically orientates the image of the camera.

18 Claims, 3 Drawing Sheets

OPERATING LAMP ASSEMBLY COMPRISING AN AUTOMATICALLY ORIENTABLE CAMERA

CROSS-REFERENCE TO RELATED APPLICATION

The present application claims priority to German Patent Application No. 10 2021 111 459.4, filed May 4, 2021. The entire contents of the above-listed application are hereby incorporated by reference for all purposes.

TECHNICAL FIELD

The present disclosure relates to an operating lamp assembly, which comprises at least one operating lamp having at least one camera.

BACKGROUND

An operating theatre is frequently equipped with a camera orientated onto the operating field, wherein the image of the camera is transferred onto a monitor in the operating theatre or in an external room, for example for training purposes. As a result, the operating field can also be made visible for people who do not have a direct view into the operating field. It is likewise conceivable for the image of the camera to be of use to the surgeon when performing the operation. Furthermore, the image of the camera can be displayed for documentation purposes.

SUMMARY

It is conventional to provide the camera on an operating lamp, wherein the operating lamp serves to illuminate the operating field. However, when orientating the operating lamp initially no notice is taken of the orientation of the camera. This may lead to the undesired situation of the image of the camera not corresponding to the desired orientation, for example of a viewing direction of the surgeon, and the operating field being shown distorted. The image may be on its head for example. This makes it orientation on the image of the camera virtually impossible.

In order to solve this problem, the camera was or is hitherto orientated manually. A disadvantage in this case is that, in addition to the manual orientation of the operating lamp, additional manual orientation of the camera is required.

The object of the present disclosure is therefore that of providing an improved operating lamp assembly.

This object is achieved by an operating lamp assembly, and/or a set composed of an operating lamp assembly and a symbol, and/or a method for operating an operating lamp assembly.

The present disclosure comprises, in a first aspect, an operating lamp assembly, which comprises at least one operating lamp for illuminating an operating field, having at least one camera for acquiring an image of the operating field. A controller of the operating lamp assembly is designed such that an image of the camera is automatically orientated.

Automatic orientation of the image makes it possible to avoid the outlay required hitherto for manual orientation. It is furthermore possible for example to avoid the situation where the observer of the image cannot orientate himself towards the image on account of an incorrectly orientated camera. Furthermore, the problem arising in the case of manual orientation, that either a controller has to be provided in the sterile region, or the surgeon cannot orientate the camera himself, is overcome.

In a possible embodiment of the present disclosure, the camera is arranged on the operating lamp, in particular on a handhold of the operating lamp.

In a possible embodiment of the present disclosure, the camera is arranged on a carrier system of the operating lamp assembly.

In a possible embodiment of the present disclosure, the orientation of the optical main axis of the camera relative to the optical main axis of the operating lamp is not automatically adjustable. Optionally, however, an orientation of the optical main axis of the camera relative to the optical main axis of the operating lamp may be manually adjustable.

However, the present disclosure is used in operating lamp assemblies in which the orientation of the optical main axis of the camera relative to the optical main axis of the operating lamp is specified in a structurally fixed manner.

In a possible embodiment of the present disclosure, an optical main axis of the camera in parallel with or at a fixed angle with respect to the optical main axis of the operating lamp. In particular, the relative orientation of the operating lamp and the camera is selected such that the camera acquires an image of the region illuminated by the operating lamp.

In a possible embodiment of the present disclosure, the optical main axis of the camera coincides with the optical main axis of the operating lamp.

In particular, the camera can be arranged on a handhold that is arranged centrally on the operating lamp, and be orientated in the same direction as the operating lamp.

In a possible embodiment of the present disclosure, the orientation of the image of the camera is achieved by orienting the camera.

In a possible embodiment of the present disclosure, the orientation of the image of the camera is achieved by digital orientation of the image.

In particular, the orientation of the image of the camera can be achieved by means of rotating the camera about at least one axis.

In a possible embodiment of the present disclosure, the orientation of the image of the camera is achieved by means of rotating the camera about the optical main axis thereof.

In a possible embodiment of the present disclosure, the orientation of the image of the camera is achieved by means of digital rotation of the image, in particular by means of digital rotation of the image in the image plane or about an axis which is perpendicular on the image plane.

In a possible embodiment of the present disclosure, the operating lamp assembly comprises a drive which can be actuated by means of the controller such that it brings about an orientation of the camera, in particular a rotation of the camera about the optical main axis thereof, such that the image of the camera is orientated.

In a possible embodiment of the present disclosure, the drive is arranged on the operating lamp.

In a possible embodiment of the present disclosure, the drive is integrated in the operating lamp.

In particular, the drive can be arranged in the handhold of the operating lamp, and the camera can rotate about the optical main axis thereof, which coincides with the optical main axis of the operating lamp.

In a possible embodiment of the present disclosure, the controller determines an orientation of the camera by means of an inclination sensor.

In a possible embodiment of the present disclosure, the inclination sensor is provided on the operating lamp.

In a possible embodiment of the present disclosure, the inclination sensor is provided on a carrier system of the operating lamp assembly.

The inclination sensor ascertains the inclination with respect to the vertical direction specified by gravity, and therefore determines an absolute orientation of the element on which it is arranged, in space, in particular the absolute orientation of the operating lamp.

In a possible embodiment of the present disclosure, the controller determines an orientation of the camera by means of an object detection means for detecting objects in the image of the camera.

In a possible embodiment of the present disclosure, the controller determines a target orientation, in at least one operating mode, on the basis of signals of an inclination sensor, and automatically orientates the image accordingly.

In a possible embodiment of the present disclosure, in the target orientation, the image of the camera is orientated such that an upper edge of the image of the camera is orientated so as to be in parallel with the horizontal.

In a possible embodiment of the present disclosure, the controller determines a target orientation, in at least one operating mode, by means of an object detection means, and automatically orientates the image accordingly.

In a possible embodiment of the present disclosure, the object detection means detects one or more objects in the image of the camera.

In particular, the object detection means may comprise image recognition software stored in memory. In particular, the object detection means may be image recognition software stored in memory and configured to processes image data.

In a possible embodiment of the present disclosure, the object is a symbol, in particular an arrow, which defines a direction, wherein the controller automatically orientates the image according to said direction.

In a possible embodiment of the present disclosure, when the image of the camera is in the target orientation, the direction of the symbol corresponds to a direction from an upper edge to a lower edge of the image.

In a possible embodiment of the present disclosure, when the image of the camera is in the target orientation, the direction of the symbol corresponds to the vertical of the image.

In a possible embodiment of the present disclosure, the symbol is deposited on a patient, beside an operating field, and/or arranged on a medical instrument.

In a further possible embodiment of the present disclosure, the object is a person, in particular a surgeon.

In a possible embodiment of the present disclosure, the controller automatically orientates the image according to a viewing direction of the person and/or a gesture of the person.

In a further possible embodiment of the present disclosure, the object is a medical instrument and/or an assembly composed of a plurality of medical instruments, for example one or more retractors, wherein the controller orientates the image according to the orientation of the instrument and/or of the assembly of a plurality of medical instruments.

In a further possible embodiment of the present disclosure, the object detection means identifies an OP situation, wherein the controller orientates the image in accordance with the identified OP image.

For example, the people involved and their arrangement around the patient are identified, and the image is orientated according to a target orientation for the identified OP situation. A plurality of OP situations, together with respective target orientations of the image, may be stored in the controller. In a possible embodiment of the present disclosure, in at least one operating mode the image can be orientated manually, and/or in at least one operating mode the controller orientates the image on the basis of signals of a manually operable input device.

Furthermore, in at least one operating mode the image may be manually orientable, wherein the manual orientation takes place independently of the controller, in particular by manual rotation of the camera.

In a possible embodiment of the present disclosure, the operating lamp assembly has at least two operating modes, wherein in a first operating mode the orientation of the image takes place automatically, and in a second operating mode the orientation of the image takes place manually. In the first operating mode, the orientation can take place on the basis of signals of an inclination sensor and/or by means of an object detection means.

In a possible embodiment, the controller is designed such that an operator can select among a plurality of different operating modes for automatic and/or manual orientation of the image.

In particular, the operating lamp assembly can be designed such that it is possible to select from at least two operating modes, by means of manual operation of an input device.

In a second aspect, the present disclosure comprises a set composed of an operating lamp assembly and a symbol which is detected by an object detection means of the controller and is consulted for orientating the image, wherein the symbol may constitute a sterilisable element.

In particular, the symbol may be a single-use product.

In a third independent aspect, the present disclosure comprises a method for operating an operating lamp assembly, wherein the operating lamp assembly comprises at least one operating lamp and at least one camera. The method comprises the following steps:

illuminating an operating field by means of the operating lamp;

recording an image of the operating field by means of the camera; and automatically orientating the image of the camera, in particular by rotating the image of the camera, in particular by automatic rotation about a main axis of the camera.

In a possible embodiment of the present disclosure, the automatic orientation is performed by means of an inclination sensor and/or an object detection means for automatically orientating, in particular rotating, the image of the camera by means of the controller.

The method may be performed as has already been described in view of the operating lamp assembly according to the disclosure.

BRIEF DESCRIPTION OF THE FIGURES

The present disclosure will now be explained in greater detail with reference to drawings and embodiments.

In the drawings.

DETAILED DESCRIPTION

Figure 1:
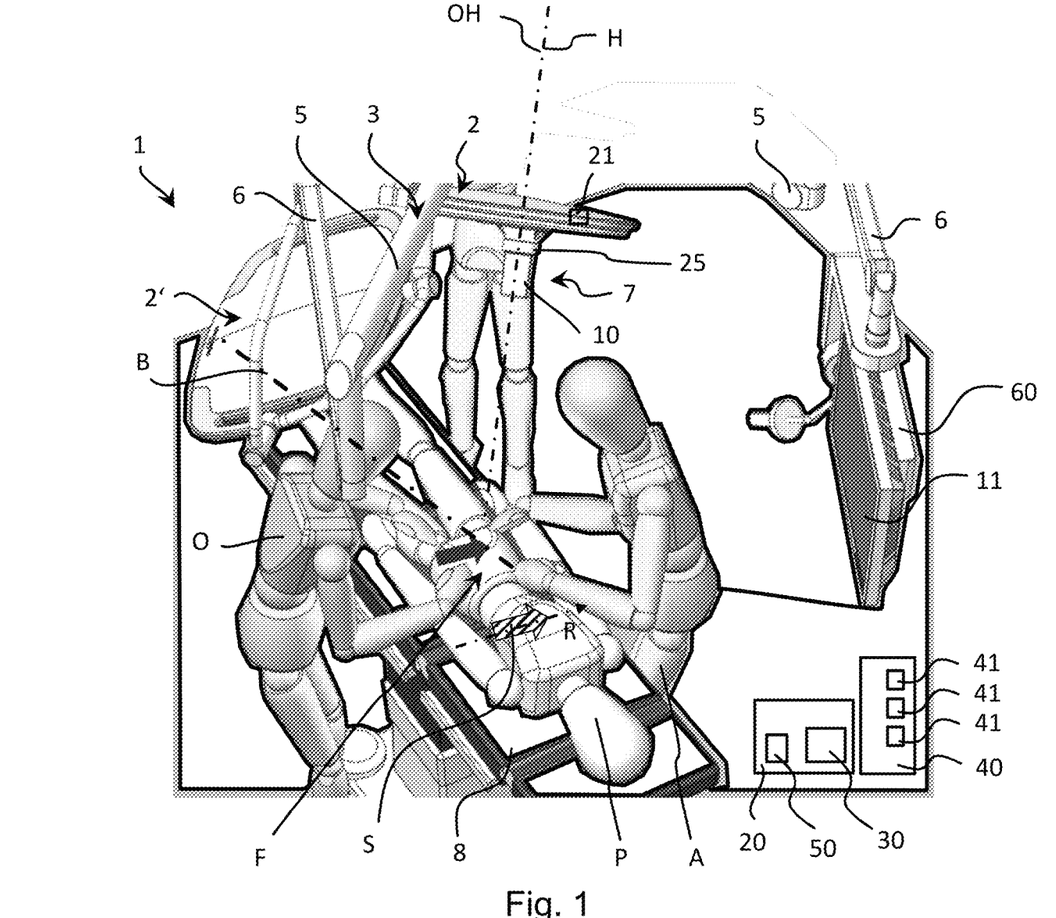
FIG. 1 shows an embodiment of an operating lamp assembly according to the disclosure comprising a camera.
Figure 2:
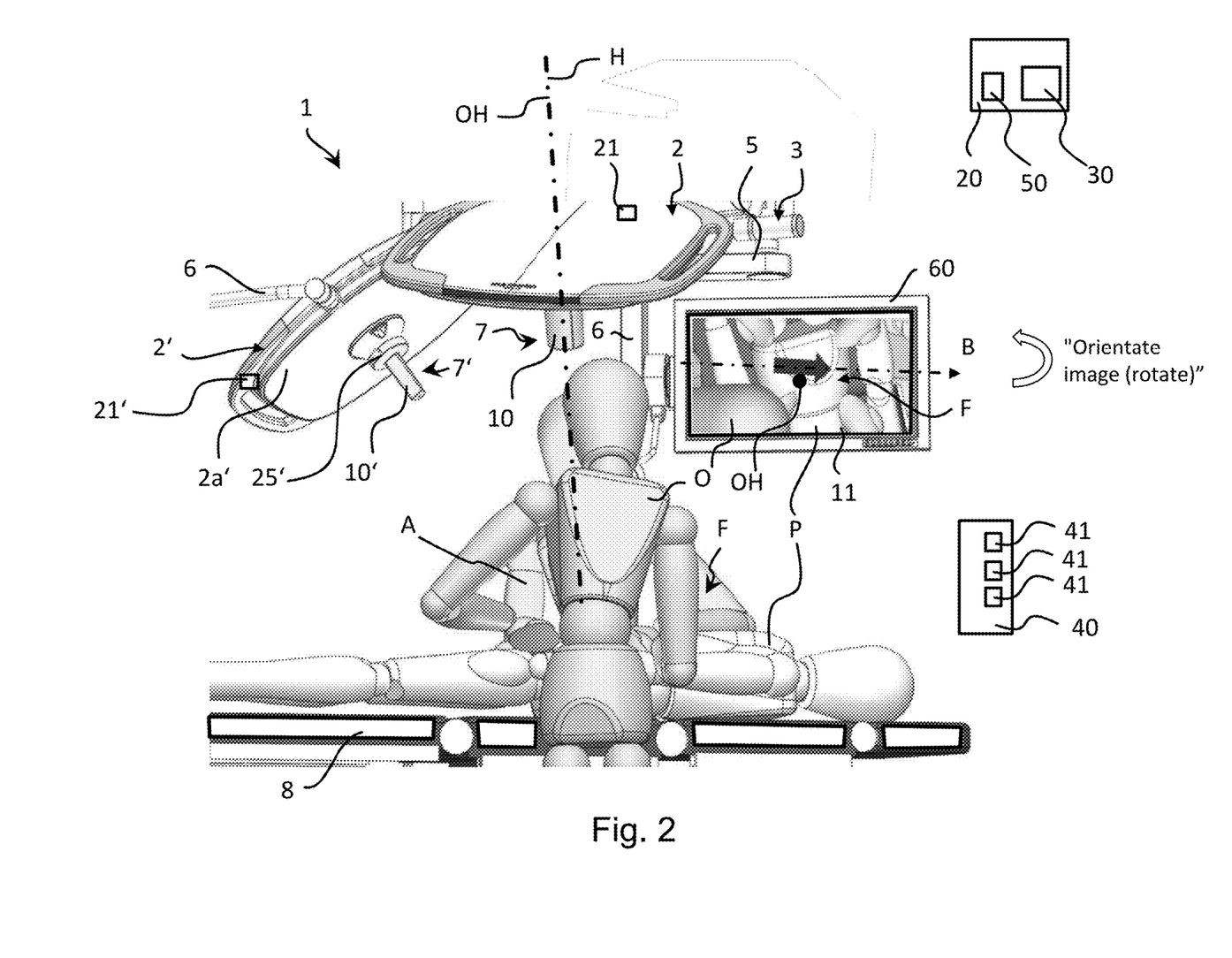
FIG. 2 shows the embodiment of an operating lamp assembly according to the disclosure shown in FIG. 1, wherein an image, which was acquired by the camera, is displayed in a distorted orientation.
Figure 3:
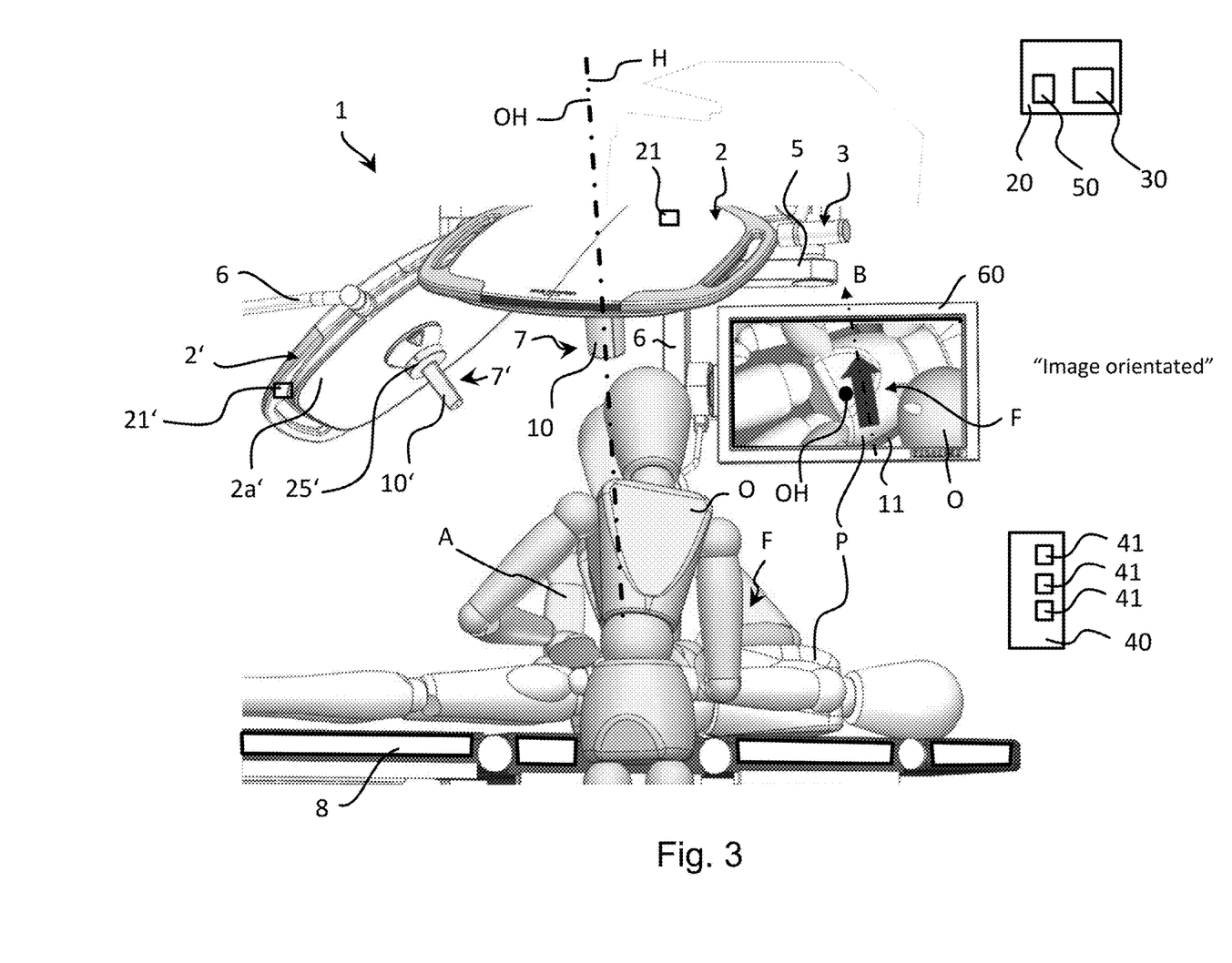
FIG. 3 shows the embodiment from FIG. 2, wherein the image has been orientated according to a target orientation.

FIG. 1 to FIG. 3 each show an embodiment of an operating lamp assembly 1 according to the disclosure, comprising a first operating lamp 2 and a second operating lamp 2'. However, within the scope of the present disclosure, the operating lamp assembly 1 could also comprise just one operating lamp 2 or more than two operating lamps 2.

In the respective embodiments, a carrier system 3 is provided, on which the operating lamps 2 and 2' are arranged above an operating table 8. The position and orientation of the operating lamps 2 and 2' can be adjusted. An adjustment can take place manually. Furthermore, an adjustment can be achieved by means of one or more drives of the carrier system 3.

In the respective embodiments, the carrier system 3 comprises a ceiling mount (not shown), on which a central shaft (not shown) can be arranged. Carrier arms 5 can in turn be pivotably arranged on the central shaft, wherein the carrier arms may be pivotable about a vertically extending axis formed by the central shaft. The operating lamps 2 and 2' can be arranged on different carrier arms 5 in each case, by means of further carrier arm elements 6 and/or joints. Embodiments of the carrier system 3 other than those just described are also conceivable.

The operating lamps 2 and 2' shown in FIG. 1 to FIG. 3 each generate a light field. The operating lamps 2 and 2' can now be orientated and/or positioned such that an operating field F of a patient P, lying on the operating table 8, is illuminated as desired. In other cases, the light fields of the two operating lamps 2 and 2' can also be orientated on different regions. This is conceivable for example in the case of a transplant, wherein an operating lamp 2 can be directed onto the operating field F, while an operating lamp 2' can be directed onto the organ to be transplanted.

In the embodiment shown in FIGS. 1 to 3, the operating lamps 2 and 2' comprise a handhold 7 and 7' for positioning and orientating the respective operating lamps 2 and 2'. In FIG. 1, only the handhold 7 of the operating lamp 2 is visible. In the embodiment of FIG. 1, the handhold 7 is arranged centrally on the operating lamp 2. The handhold 7 is in particular arranged centrally on a lamp body and surrounded by light-emitting regions of the lamp. The main axis of the handhold 7 and 7', respectively, may correspond to the optical main axis of the lamp 2 and 2', respectively.

The handhold 7 and 7', respectively, can furthermore, as shown in the embodiments shown in FIGS. 1 to 3, be arranged in the geometric centre of a light source 2a' of the corresponding operating lamp 2 and 2', respectively, that generates the light field. As shown in FIGS. 1 to 3, the operating lamp 2 and 2', respectively, can also comprise one or more handhold elements, which are arranged laterally on the operating lamp 2 and 2', respectively. The handhold elements can be provided as an alternative to or in addition to the handhold 7 and 7'.

In the embodiment shown in FIGS. 1 to 3, the operating lamp assembly 1 comprises a camera 10 for generating an image 11, wherein the operating lamp assembly 1 further comprises a monitor 60 for displaying the image 11 of the camera 10. The camera 10 is arranged on the first operating lamp 2.

In a first variant, the operating lamp 2' does not comprise a camera.

In contrast, in a second variant, the operating lamp assembly 1 comprises two cameras 10 and 10', which are arranged correspondingly on the operating lamps 2 and 2'.

The monitor 60, as well as the operating lamps 2 and 2', can be arranged on the carrier system 3 by means of a carrier arm element 6. In the embodiments shown in FIGS. 1 to 3, the monitor 60 is located in the operating theatre. It is also conceivable, however, for the monitor 60 or another monitor to be provided in a room that is separate from the operating theatre. In this way, the image 11 of the camera 10 can be made available for example for training purposes. It is also conceivable to supply the image of the camera to a memory unit, and record it there, for documentation purposes.

Within the meaning of the present disclosure, the term "image" includes both a video image within the meaning of an image sequence, and an individual image within the meaning of a photograph.

In a possible embodiment of the present disclosure, the image is a video image.

As shown in FIGS. 1 to 3, in the embodiment the optical main axis OH of the camera 10 and the optical main axis H of the operating lamp 2 are orientated so as to be mutually parallel, and furthermore coincide. As shown in FIGS. 1 to 3, the optical main axis H of the operating lamp 2 can extend through a geometric centre of the operating lamp 2, in particular through a geometric centre of a light source of the operating lamp 2, in particular through a centre point of the operating lamp 2.

Viewed along the main axis thereof, the operating lamp 2, in particular the light source thereof, can be rectangular and/or round in shape, and/or is formed in a plate-shaped manner.

As shown in FIGS. 1 to 3, the optical main axis H of the operating lamp 2 corresponds to a central axis of a light cone generated by the light source. If both operating lamps 2, 2' each comprise a camera 10, 10', the optical main axis of the relevant camera 10, 10' may coincide with the optical main axis of the relevant operating lamp 2'.

According to the present disclosure, the operating lamp assembly comprises a controller which is designed such that an image of the camera is automatically orientated.

In FIGS. 1 to 3, the relevant operating lamp assembly 1 comprises a controller 20, by means of which the image 11 of the camera 10, 10' is automatically orientated. This can be achieved by means of orientating the camera 10 or 10', and/or by means of digitally orientating the image 11 and 11', respectively, of the camera 10 and 10', respectively. The digital orientation of the image 11 or 11' can be achieved by means of the controller 20, in particular by means of an arithmetic unit 50, which may be integrated in the controller 20. The relevant operating lamp 2 can be linked to the controller 20 and/or the input device 40 in a wired and/or wireless manner.

The orientation of the image 11 may be achieved by means of orientating the camera 10, 10', i.e. b means of mechanical orientation of the camera 10, 10', wherein the mechanical orientation may be achieved by means of the drive 25, 25' which is shown in FIG. 1 for example. In the embodiment shown in FIGS. 1 to 3, the drive 25 is arranged on the operating lamp 2. In particular, the drive 25 can be integrated into the handhold 7 of the operating lamp 2, as shown in FIG. 1. By means of the controller 20, the drive 25, 25' can be actuated such that the camera 10, 10' is orientated according to a target orientation of the image 11, 11'.

In the embodiment, the camera 10, 10' can be rotated about the optical main axis OH thereof, in order to orientate the image 11. For this purpose, the controller 20 actuates the drive 25, 25' such that a target orientation of the image 11, 11' of the camera 10, 10' is achieved by means of the orientation of the camera 10, 10'.

Alternatively or in addition, the automatic orientation of the image 11 or 11' can be achieved by means of digitally orientating the image 11 or 11', in particular by rotating the image in the image plane.

The automatic orientation of the image can take place in different manners:

In a first embodiment, the controller 20 determines the orientation of the camera 10, 10' on the basis of signals of an inclination sensor 21. The inclination sensor 21 can be arranged on the operating lamp 2, 2', as shown for example in FIGS. 1 to 3. It is also conceivable, however, to provide the inclination sensor 21 at another location, for example on the carrier arm 5. The inclination sensor 21 may be a digital and/or electronic spirit level.

The image 11 or 11', respectively, may be orientated on the basis of the inclination sensor 21 or 21', respectively, such that an upper edge of the image 11 or 11', respectively, is orientated so as to be in parallel with a horizontal.

In a second embodiment, an object detection means 30 is provided, by means of which the controller 20 can determine the orientation of the image 11, 11' of the camera 10, 10', as is shown for example in FIGS. 1 to 3. The automatic orientation of the image 11 or 11' then takes place into a target orientation determined on the basis of the object detection means 30.

The object detection means 30 may be image recognition software stored in memory for example. The controller 20 may comprise the object detection means 30, in particular the object detection means 30 may be an integral component of the controller 20. However, the object detection means 30 may also be provided separately from the controller 20. The object detection means 30 can be actuated such that it can detect one or more objects in the image 11 of the camera 10 or in the image 11' of the camera 10'.

The object detection means 30 can have one or more of the following functions:

a. The OP situation is identified by means of the acquired image 11 or 11', respectively, of the camera 10 or 10', respectively, and the image 11 or 11', respectively, is then orientated. For example, the people O and/or A involved and their arrangement around the patient P are identified, and the image 11 or 11' is orientated according to a target orientation for the identified OP situation. A plurality of OP situations, together with respective target orientations of the image 11 or 11', can be stored in the controller 20.

b. The surgeon O is identified by means of the acquired image 11 or 11', respectively, and the image 11 or 11', respectively, is orientated according to the surgeon's viewing direction. It is in particular possible to identify on which side of the operating field F the surgeon O is located, and the image 11 and/or 11' is orientated such that the vertical of the image 11 and/or 11 corresponds to a connecting line between the position of the surgeon O and the operating field F. In this case, the direction of the connecting line between the position of the surgeon O and the operating field F can be defined as the viewing direction of the surgeon O. Alternatively, the actual viewing direction of the surgeon can be identified, and can form the basis of the automatic orientation.

c. A medical instrument (e.g. retractor, clamp or endoscope) is identified by means of the acquired image 11 or 11', respectively, and the image 11 or 11', respectively, is orientated according to the direction and/or position of said instrument.

d. An accessory/tool is identified by means of the acquired image 11 or 11', respectively, according to which accessory/tool the image 11 or 11', respectively, is intended to be orientated. This may for example be a direction pointer, which may be designed so as to be sterilizable or as a single-use product. Alternatively, the orientation of a passive panel, which is in any case detected for actuating the light assembly 1 and/or other devices in the operating theatre, which is consulted for orientating the image 11 or 11', respectively, of the camera 10 or 10', respectively.

The passive panel according to variant d) may in particular be a passive operating panel, as is known from DE 10 2020 114 426 by the applicant. The operating panel may be a passive, sterile and/or sterilizable element. At least one symbol may be provided on the operating panel, by means of which symbol operator inputs can be performed on the operating panel. The operating panel may be a completely passive operating panel, i.e. it does not have any electronic components or a power supply. It may be produced from a sterilizable plastics material or stainless steel. On account of these properties, it is sterilizable without problem, and is prepared in a sterilized manner just like the normal instruments such as scalpels, clamps, scissors, etc. On account of the very simple structure, a single-use variant is also conceivable.

In points a.-d., the evaluation takes place by means of image recognition. Resulting herefrom, the drive 25 or 25', respectively, of the camera 10 or 10', respectively, is controlled, and the image 11 or 11', respectively, is automatically orientated. It is also possible to digitally orientate/ rotate the image 11 or 11', respectively, and no drive 25 or 25', respectively, is required for this purpose. The rotation is then performed exclusively digitally.

As shown in FIG. 1, according to variant d), in addition to the operating field F, a symbol S, which, as shown, may be an arrow, can be provided. In the embodiment, the object detection means 30 detects the symbol S in the image 11 of the camera 10, and determines the orientation of the camera 10 and/or the orientation of the image 11 on the basis of the orientation R of the symbol S. The controller 20 then orientates the image 11 of the camera 10 in accordance with a target orientation, on the basis of the determined orientation R of the symbol S. The symbol S can for example also be provided on a medical instrument. For example, the image 11 can be orientated such that the symbol S points in a defined direction, for example upwards.

FIG. 2 shows an image 11 of the camera 10 in an orientation which does not correspond to its target orientation. In contrast, FIG. 3 shows an image 11 of the camera 10 which is orientated in accordance with a target orientation. The image 11 shown in FIG. 3 was obtained by means of orientation according to the disclosure, in particular rotation, of the image 11 shown in FIG. 2. The rotation of the image 11 can be preformed by rotating the camera 10 or by digital rotation of the image of the camera.

In a second variant, the object detection means 30 detects the surgeon O on the image 11 of the camera 10. In particular, the object detection means 30 can detect the viewing direction B of the surgeon O, wherein the image 11 of the camera 10 is orientated according to the viewing direction B, by means of the controller 20. It is also conceivable for the image 10 of the camera 11 to be orientated according to a detected gesture of the surgeon O.

The images 11 and 11 shown in FIG. 2 and FIG. 3 in each case show an operating field F, wherein the viewing direction B of the surgeon O is illustrated by means of an arrow. Furthermore, a patient P is shown.

The optical main axis OH of the camera, by means of which the image 11 was acquired, extends in both figures perpendicularly with respect to the image plane of the display, and thus with respect to the drawing plane in the figures. As shown in FIGS. 2 and 3, the optical main axis OH of the camera, about which the image is rotated, can extend through the geometric centre, in particular the centre point, of the image 11.

The orientation/rotation of the image 11 can be preformed for example by rotating the camera 10 and/or by means of digital rotation of the image 11 of the camera 10.

In the embodiment shown in FIG. 3, the target orientation corresponds to an orientation of the image 11 in which the viewing direction B of the surgeon O detected by the image detection means 30 extends from a lower edge to an upper edge of the image 11.

The operating lamp assembly may have a plurality of operating modes, in which the automatic orientation take place in each case on the basis of different criteria. The criterion to be used in each case can be selectable by an operator of the operating lamp assembly.

The embodiment of the operating lamp assembly 1 shown in FIGS. 1 to 3 has a first operating mode, in which the orientation of the image 11, 11' takes place automatically on the basis of signals of the inclination sensor 21. In the embodiment, the operating lamp assembly 1 furthermore has a second operating mode, in which the orientation of the image 11 takes place automatically, by means of the object detection means 30. In the embodiment, the operating lamp assembly 1 has a third operating mode, in which the orientation of the image 11 takes place manually.

In an embodiment of the operating lamp assembly 1 comprising two cameras 10 and 10', the orientation of the respective images 11, 11' can take place in a mutually independent manner, according to different operating modes or according to a common operating mode.

In the first operating mode of the operating lamp assembly 1 shown in FIGS. 1 to 3, the controller 20 thereof determines the orientation of the camera 10 by means of the inclination sensor 21 which is arranged on the operating lamp 2. On the basis of the signals of the inclination sensor 21, the controller 20 determines a target orientation of the image 11 and automatically orientates the image 11 accordingly.

In the second operating mode of the operating lamp assembly 1 shown in FIGS. 1 to 3, the orientation of the image 11 is determined by means of the object detection means 30. A target orientation of the image 11 is determined by the object detection means 30, wherein the image 11 is automatically orientated accordingly.

The second operating mode may comprise a plurality of sub-modes, which differ with respect to the criteria according to which an automatic orientation takes place on account of the object detection means 30. In particular, depending on the sub-mode, the automatic orientation can take place on the basis of various criteria evaluated by the object detection means, in particular on the basis of the criteria a) to d) above.

Both in the first and in the second operating mode, the automatic orientation of the image 11 by means of the controller 20 can take place by actuating the drive 25, and a mechanical orientation of the camera 10 which corresponds thereto.

In the embodiment, for this purpose the camera 10 is rotated about the optical main axis OH thereof, such that the orientation of the camera 10 corresponds to the relevant target orientation of the image 11 of the camera 10.

Alternatively or in addition, the automatic orientation of the image 11 can be achieved by means of digital orientation, in particular rotation, of the image 11. The digital orientation of the image 11 can be achieved by means of the controller 20, in particular by means of an arithmetic unit 50 of the controller 20. Alternatively, the digital orientation of the image 11 can also be achieved by means of an arithmetic unit 50 which may be provided separately from the controller 20. The controller 20 can communicate with the arithmetic unit 50 wirelessly and/or in a wired manner.

The controller may include a processor and memory with instructions stored therein to carry out the operations described herein. The arithmetic unit may include a processor and/or application specific integrated circuit (ASIC) programmed to carry out arithmetic operations as described herein.

In the third operating mode of the operating lamp assembly 1 shown in FIGS. 1 to 3, the orientation of the image 11 takes place manually. In the embodiment, this takes place by means of manual actuation of the input device 40.

In the embodiment, the input device 40 communicates with the controller 20, wherein the controller 20 orientates the image 11 on the basis of signals of the input device 40. The manual orientation of the image 11 can take place by means of orientating the camera 10, in particular rotating the camera 10 about the optical main axis OH thereof, and/or by means of digitally orientating the image 11, in particular by means of rotating the image 11 about the optical main axis OH thereof.

It is also conceivable to design the operating lamp assembly 1 such that, in one operating mode, manual orientation of the image 11 takes place in combination with automatic orientation of the image 11. In an operating mode of this kind, the controller 20 could tailor the two types of orientation to one another. It would be conceivable, for example, for manual orientation of the image 11 to be used only for readjustment, for example after automatic orientation of the image 11 has taken place.

An operator can select among the different operating modes of the operating lamp assembly.

An operator can select among different operating modes of the operating lamp assembly such that at least two images of different cameras are orientated in accordance with different operating modes or in accordance with a common operating mode.

In order to switch among the different operating modes, the input device 40 shown in FIGS. 1 to 3 may be provided, by means of the manual operation of which the different operating modes can be selected.

For this purpose, the input device 40 shown in FIGS. 1 to 3 may comprise at least one input element 41. In the embodiments shown in FIGS. 1 to 3, the input device 40 is furthermore designed such that the manual orientation of the image 11 takes place by means of the manual actuation of the input device 40. For this purpose, corresponding input elements 41 may be provided on the input device 40, which elements may be provided for example in the form of switches, adjusters, and/or a touch screen. For example, a first input element 41 for rotating the image 11 to the left, about the optical main axis thereof, and a second input element for rotating the image 11 to the right, about the optical main axis thereof, may be provided. In an example, the input element may be a button or knob.

If two cameras 10 and 10' are provided, the relevant orientation of the images 11, 11' can take place as already described above.

In an embodiment of the present disclosure, the images 11, 11' of the two cameras 10 and 10' are automatically orientated such that they show the operating field F in the same orientation.

Furthermore, the operating lamp assembly 1 may be designed such that it is possible to manually select, by means of the input device 40, what image 11, 11' or what images are displayed on the monitor 60. For example, it is thus possible for at least one image, from the images 11 and 11', to be selected for display on the monitor 60, by means of manual actuation of the input device 40. The images can for example also be arranged side-by-side on the monitor 60.

LIST OF REFERENCE SIGNS 1 operating lamp assembly
2, 2' operating lamp
2a' light source of the operating lamp 2'
3 carrier system
5 carrier arm
6 carrier arm element
7 handhold
8 operating table
10, 10' camera
11, 11' image of the camera
20 controller
21 inclination sensor
25 drive
30 object detection means
40 input device
41 input elements
50 arithmetic unit
60 monitor
F operating field
OH optical main axis of the camera 10
H optical main axis of the operating lamp 2
S symbol
R direction
O surgeon
B viewing direction
A assistant
P patient

The invention claimed is:

1. An operating lamp assembly which comprises at least one operating lamp for illuminating an operating field, having at least one camera for acquiring an image of the operating field,
wherein
the operating lamp assembly comprises a controller which automatically orientates the image of the camera,
wherein the controller determines an orientation of the camera by means of an inclination sensor which is provided on the operating lamp and/or on a carrier system of the operating lamp assembly, and/or wherein the controller determines an orientation of the camera by means of an object detection means for detecting objects in the image of the camera.

2. The operating lamp assembly according to claim 1, wherein the camera is arranged on the operating lamp, or wherein the camera is arranged on a carrier system of the operating lamp assembly.

3. The operating lamp assembly according to claim 1, wherein an optical main axis of the camera extends in parallel with or at a fixed angle with respect to an optical main axis of the operating lamp.

4. The operating lamp assembly according to claim 3, wherein orientation of the image of the camera takes place by means of orientating the camera and/or by means of digitally orientating the image.

5. The operating lamp assembly according to claim 3, further comprising a drive which can be actuated by means of the controller such that it brings about an orientation of the camera.

6. The operating lamp assembly according to claim 3, wherein the optical main axis of the camera coincides with an optical main axis of the operating lamp, and/or wherein an orientation of the optical main axis of the camera with respect to the optical main axis of the operating lamp is specified in a structurally fixed manner and/or is not automatically adjustable.

7. The operating lamp assembly according to claim 4, wherein the orientation of the image of the camera takes place by means of rotating the camera about the optical main axis thereof and/or by means of digitally rotating the image in an image plane.

8. The operating lamp assembly according to claim 5, wherein the camera rotates about the optical main axis such that the image of the camera is orientated.

9. The operating lamp assembly according to claim 1, wherein the controller determines a current orientation of the camera and/or a target orientation of the image, wherein the controller automatically orientates the image in accordance with the current orientation of the camera and/or the target orientation of the image.

10. An operating lamp assembly which comprises at least one operating lamp for illuminating an operating field, having at least one camera for acquiring an image of the operating field,
wherein
the operating lamp assembly comprises a controller which automatically orientates the image of the camera, wherein, in at least one operating mode, the controller determines a target orientation on the basis of signals of an inclination sensor and automatically orientates the image accordingly.

11. The operating lamp assembly according to claim 10, wherein, in the target orientation, the image of the camera is orientated such that an upper edge of the image of the camera is orientated so as to be in parallel with the horizontal.

12. The operating lamp assembly according to claim 10, wherein, in at least one operating mode, the image can be orientated manually, and/or wherein, in at least one operating mode, the controller orientates the image on the basis of signals of a manually operable input device.

13. The operating lamp assembly according to claim 10, wherein the operating lamp assembly has at least two operating modes, wherein, in a first operating mode, the orientation of the image takes place automatically, and in a second operating mode the orientation of the image takes place manually.

14. An operating lamp assembly which comprises at least one operating lamp for illuminating an operating field, having at least one camera for acquiring an image of the operating field,
wherein
the operating lamp assembly comprises a controller which automatically orientates the image of the camera, wherein, in at least one operating mode, the controller determines a target orientation by means of an object detection means and automatically orientates the image accordingly.

15. The operating lamp assembly according to claim 14, wherein the object is a symbol which defines a direction, and the controller automatically orientates the image according to said direction, and/or wherein an OP situation is identified by the object detection means, wherein the controller orientates the image in accordance with the identified OP situation.

16. The operating lamp assembly according to claim 14, wherein the object is a person, wherein the controller orientates the image in accordance with a viewing direction of the person and/or a gesture of the person, and/or wherein the object is a medical instrument and/or an assembly composed of a plurality of medical instruments, wherein the controller orientates the image in accordance with the orientation of the instrument or of the assembly of instruments.

17. The operating lamp assembly according to claim 14, wherein the object detection means detects one or more objects in the image of the camera.

18. A set composed of an operating lamp assembly and a symbol, wherein the operating lamp assembly comprises at least one operating lamp for illuminating an operating field, having at least one camera for acquiring an image of the operating field,
- wherein the operating lamp assembly comprises a controller which automatically orientates the image of the camera, and
- wherein the symbol is detected by an object detection means of the controller and is consulted for orientating the image.

* * * * *